United States Patent
Lundbäck et al.

(10) Patent No.: US 7,239,987 B2
(45) Date of Patent: Jul. 3, 2007

(54) COMPUTER BASED SYSTEM ADAPTED TO CREATE A REPRESENTATION OF THE PUMPING ACTION OF A HEART

(75) Inventors: Stig Lundbäck, Vaxholm (SE); Anders Edfors, Stockholm (SE); Jonas Johnsson, Norrtälje (SE)

(73) Assignee: GrippingHeart AB, Stockholm (SE)

( * ) Notice: Subject to any disclaimer, the term of this patent is extended or adjusted under 35 U.S.C. 154(b) by 715 days.

(21) Appl. No.: 10/276,181

(22) PCT Filed: May 17, 2001

(86) PCT No.: PCT/SE01/01095
§ 371 (c)(1),
(2), (4) Date: Apr. 10, 2003

(87) PCT Pub. No.: WO01/88642
PCT Pub. Date: Nov. 22, 2001

(65) Prior Publication Data
US 2003/0166991 A1  Sep. 4, 2003

(30) Foreign Application Priority Data
May 18, 2000  (SE) .................................... 0001836

(51) Int. Cl.
*G06F 7/60* (2006.01)
*G06F 17/50* (2006.01)
*G09B 23/28* (2006.01)

(52) U.S. Cl. .................... 703/2; 434/265; 434/266; 434/267; 434/268; 434/272

(58) Field of Classification Search ............... 703/2, 703/11; 434/265, 266, 267, 268, 272
See application file for complete search history.

(56) References Cited

U.S. PATENT DOCUMENTS

| | | | | |
|---|---|---|---|---|
| 5,151,856 | A | | 9/1992 | Halmann et al. ........... 600/508 |
| 5,732,192 | A | * | 3/1998 | Malin et al. .................... 703/2 |
| 5,860,933 | A | * | 1/1999 | Don Michael ............... 600/528 |
| 5,947,899 | A | | 9/1999 | Winslow et al. ............ 600/410 |
| 6,205,871 | B1 | * | 3/2001 | Saloner et al. ............. 73/866.4 |
| 6,801,643 | B2 | * | 10/2004 | Pieper .......................... 382/128 |

OTHER PUBLICATIONS

Silvio Cavlcanti, Stefano Severi and Claudia Boarini, "Mathematical Analysis of the Aotonomic Influence on the Heart Rate Variability", IEEE, 1996, pp. 1580-1581.*
T. Cui, J.K-J. Li W Welkowitz and S. Petrucelli, "Control Variables and Algorithms for a Series Cardiac Assistance", IEEE 1988, pp. 5-7.*
Lundbäck, Stig; "Heart Mechanics"; URL: http://www.grippingheart.com; 1999.
Cacalcanti, Silvio et al.; "Modeling of Cardio-Vascular Variability Using Differential Delay Equation"; IEEE Transactions on Biomedical Engineering; Oct. 1996, vol. 43, No. 10, pp. 982-988.

* cited by examiner

Primary Examiner—Paul Rodriguez
Assistant Examiner—Dwin McTaggart Craig
(74) Attorney, Agent, or Firm—Harness, Dickey & Pierce, P.L.C.

(57) ABSTRACT

Computer-based system adapted to create a representation of mechanical and flow-mechanical function of a δV-pump. A mathematical modeling algorithm is used based upon a transforming element adapted to connect different physical domains via a transforming value. The system comprises an upper transforming element (TF1) and a lower transforming element (TF2) each having a flow domain (fd1, fd2) and a mechanical domain (md1, md2), the upper transforming element is provided with a transforming value A1 and the lower transforming element is provided with a transforming value A1+A2, wherein A1 and A2>0. The upper and lower transforming elements are interconnected such that their mechanical domains are connected, said mechanical domains are provided with a control value representing a directional measure (F) arranged to intermittently and simultaneously activate said mechanical domains of the transforming elements. By interconnecting two δV-pump representations the pumping action of a heart may be simulated.

12 Claims, 8 Drawing Sheets

Figure 1A:
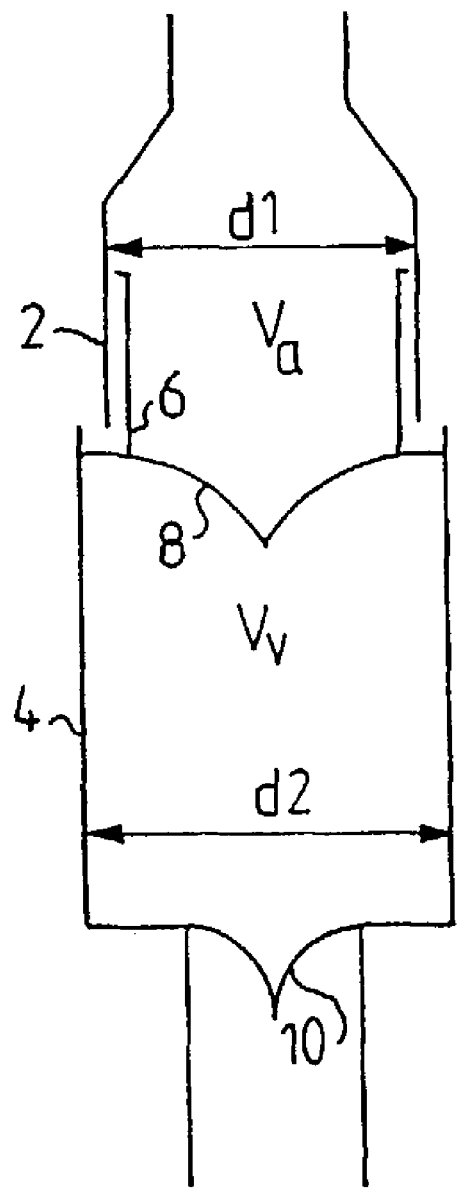

COMPUTER BASED SYSTEM ADAPTED TO CREATE A REPRESENTATION OF THE PUMPING ACTION OF A HEART

FIELD OF THE INVENTION

The invention relates to a computer-based system that is adapted to create a representation of mechanical and flow-mechanical function of a ΔV-pump using a mathematical modeling algorithm.

BACKGROUND OF THE INVENTION

It is asserted in Lundbäck S., "Cardiac Pumping and Function of the Ventricular Septum", Stockholm, 1986, that the pumping and regulation of the human heart take place in a manner which is at variance with the prevalent view. According to the cited publication, the healthy heart performs its pumping action without substantially changing its outer shape and volume. More particularly, during ventricular systole (the active, expulsive phase of the heart cycle) the so-called valve plane, that is, the plane containing the atrioventricular heart valves and the connections of aorta and pulmonary artery, is drawn towards the heart apex and forces the blood contained in the ventricles into the pulmonic and systemic circulation, and at the same time blood is drawn into the atria as a consequence of the movement of the valve plane. During ventricular diastole, the phase of the heart cycle in which the heart muscle is relaxed, the valve plane is returned to the initial position under the influence of the momentum which is imparted to the inflowing blood as a consequence of the downward movement of the valve plane during ventricular systole.

As is also asserted in the publication (on the basis of the finding that the outer volume and shape of the heart are substantially constant over the heart cycle), the ability of the heart to change the relative volumetric capacities of the right and left ventricles is attributable mainly to the common ventricular wall, the ventricular septum, namely by virtue of its flexibility in the relaxed state of the heart. During ventricular systole the ventricular septum together with the rest of the left ventricular musculature always assumes an essentially cross circular cross-sectional configuration and takes a distinct position independently of its shape and position during diastole. This is so, because during ventricular systole the pressure in the left ventricle is always higher than the pressure in the right ventricle. If the configuration and position of the ventricular septum during diastole, the relaxed state, are different from the configuration and position during systole, The active state, the ventricular septum, acting like a diaphragm pump, therefore provides an increased stroke volume for one ventricle and a correspondingly reduced stroke volume for the other ventricle, In this way, the ventricular septum accomplishes a double-acting regulation to maintain the balance between the two branches of the circulatory system (the pulmonary circulation and the systemic circulation).

As a result of the theory presented in above-mentioned publication regarding the heart's pumping and regulating function a new class of pumps has emerged, a so called dynamic displacement pump or delta (Δ) volume pump (abbreviated as ΔV-pump).

The principles of a ΔV-pump will now be described with references to FIGS. 1a and 1b.

The pump comprises an upper cylinder 2 with diameter d1 and a lower cylinder 4 with diameter d2, where d2>d1. These two cylinders are connected to each other via a third cylinder 6 that is freely movably arranged between the upper and lower cylinders. The movable cylinder 6 is provided with a valve 8 at its lowest part that corresponds e.g. to the mitralis valve in the heart. The volume above this valve is defined as the atrial volume (Va) and the volume below the valve is defined as the ventricular volume (Vv). The lower cylinder is provided with an outflow valve 10 at its lowest part that corresponds e.g. to the aortic valve in the heart. As can be seen from FIG. 1b is a ring-shaped cylindrical volume gradually obtained between the movable cylinder and the inner wall of the lower cylinder when the movable cylinder is moved down, ΔV in the figure. This results in that the volume Va+Vv decreases with the volume ΔV when the movable cylinder moves between its upper position and its lower position. A source of energy (not shown in the figures) is adapted to move the movable cylinder from its upper position to its lower position, which defines the length L of a stroke for the pump. When the movable cylinder moves down to its lowest position the outflow valve is forced to open and a part of volume Vv is expelled. The movable cylinder is then released from the source of energy and can return to its upper position. If Av and Aa designates the cross-sectional areas of the upper and lower cylinder, respectively, ΔV equals L(Av−Aa).

A short description of the behavior of the ΔV-pump when pumping with a lower frequency and with a higher frequency will here follow, with references to FIGS. 2 and 3 respectively.

Figures 2A, 2B, 2C, 2D:
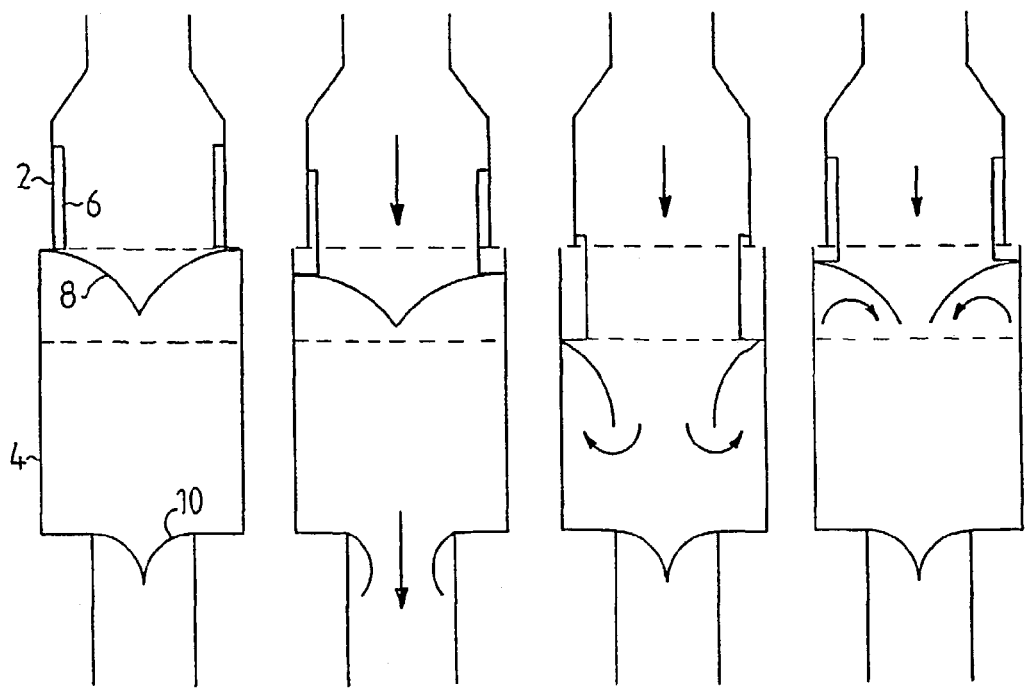

In FIGS. 2a-2d different stages of the pumping process with a low frequency are disclosed. In FIG. 2a the external force starts moving the movable cylinder down, when the pressure inside the lower cylinder exceeds the pressure below the outflow valve 10 it opens (FIG. 2b). The outflow valve closes when the pressure below the valve exceeds the pressure above. When the movable cylinder is in the lowest position the force activation ends and the fluid in the upper cylinder, which has gained kinetic energy downwards, force the valve 8 to open (FIG. 2c). The inflow in the lower cylinder creates an internal redistribution of the fluid, indicated by the arrows, that firstly forces the freely movable cylinder back to the upper position and secondly creates the necessary pressure to close the valve 8 (FIG. 2d). The reason to this is the different diameters of the upper and lower cylinders resulting in that the movable cylinder has a greater area towards volume Vv than towards volume Va. When these areas are exposed to the same pressure the force towards the upper position will be greater due to the greater area. This in turn results in that the inflow continues even when the outflow has stopped.

Figures 3A, 3B, 3C, 3D:
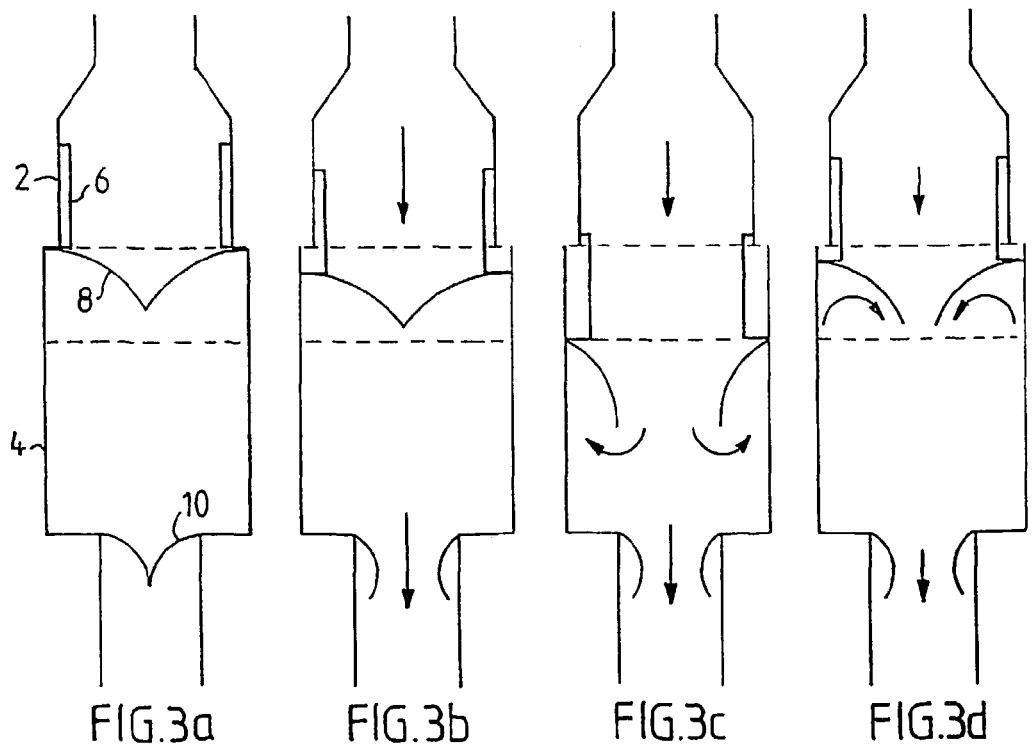

In FIGS. 3a-3d different stages of the pumping process with a high frequency are disclosed. FIG. 3a illustrates only the starting position whereas the pumping process with a high frequency is illustrated by FIGS. 3b-3d. The differences from the pumping process with a low frequency are illustrated in FIGS. 3c and 3d. The downward kinetic energy is in this case so large that both valves are opened when the movable cylinder reaches the lower position. The valves are then closed due to the same reasons as when pumping with low frequency.

Many different requirements must generally be met when implementing a mathematical model. It should preferably be module based in order to be easy to modify, to monitor, to error detect and to control. It is also important that different physical systems, such as mechanical, electrical, thermal and hydraulic systems easily can be connected together and it must be possible to control and to monitor any part of the model when at work.

In order to describe graphically a system with different physical domains the so called bond graphs has proven to be a powerful tool. Bond graphs was introduced by H. Paynter at the MIT and is e.g. described in Karnopp, Margolis, Rosenberg, "System Dynamics: A Unified Approach" (second edition) and in Thoma, Jean U. "Simulation by Bond graphs, introduction to a Graphical Method"; Springer-Verlag.

The basics for a systematic modeling using bond graphs are essentially to follow the energy flow through the system(s).

One object of the invention is to be able to simulate the function of a ΔV-pump.

One further object of the invention is to be able to simulate the functions of a heart by using a mathematical model of the functions of the heart based upon the above-described principles of the ΔV-pump in order to make it possible to enhance the methods of analyses, diagnosis and therapy of the heart.

SUMMARY OF THE INVENTION

The above-mentioned object of the invention is achieved according to characterizing portions of the independent claims. Preferred embodiments are set forth in the dependent claims.

According to a preferred embodiment of the invention the heart is modeled by a computer-based representation of one dynamic displacement pump or of two interconnected dynamic displacement pumps, ΔV-pumps.

SHORT DESCRIPTION OF THE APPENDED DRAWINGS

Figure 1B:
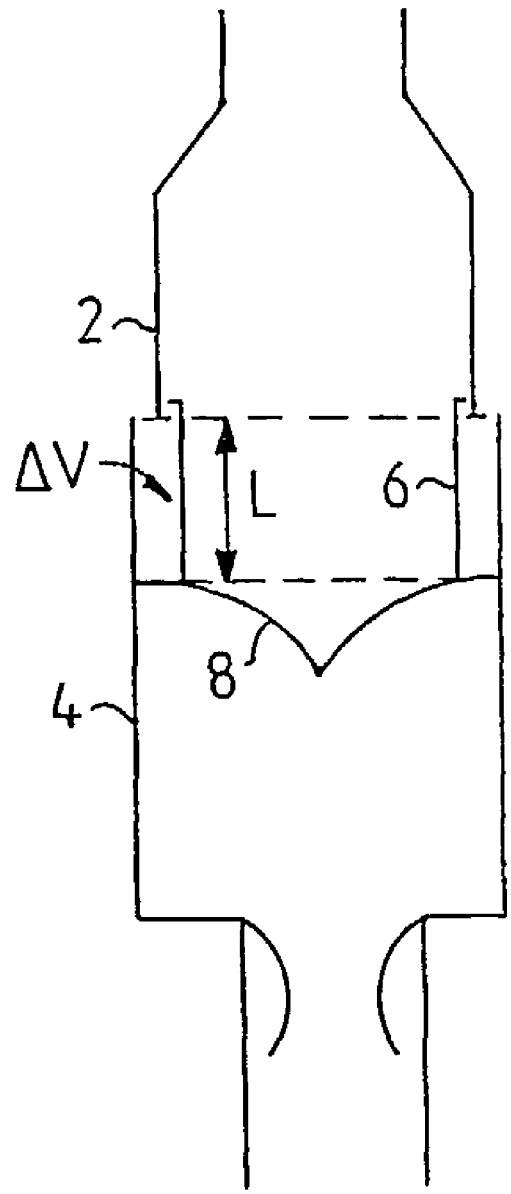
Figure 4A:
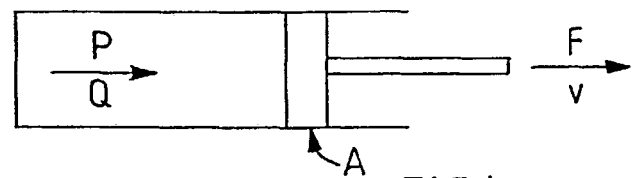
Figure 4B:
Figure 5:
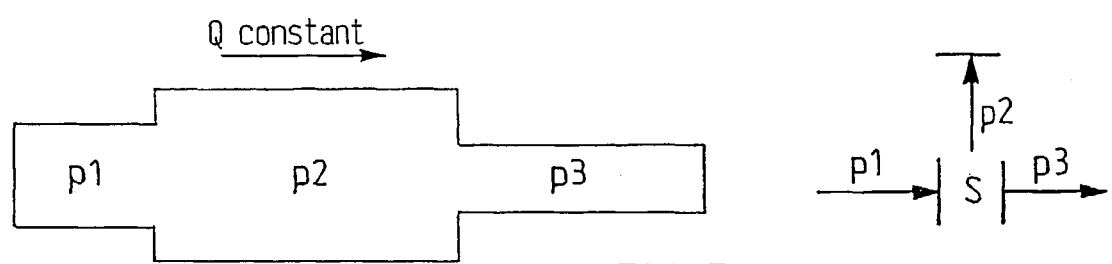
Figure 6:
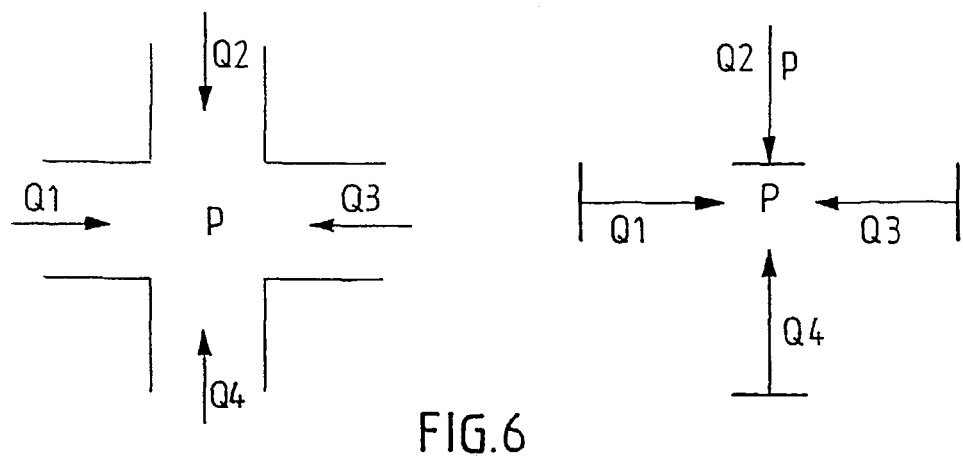
Figure 7A:
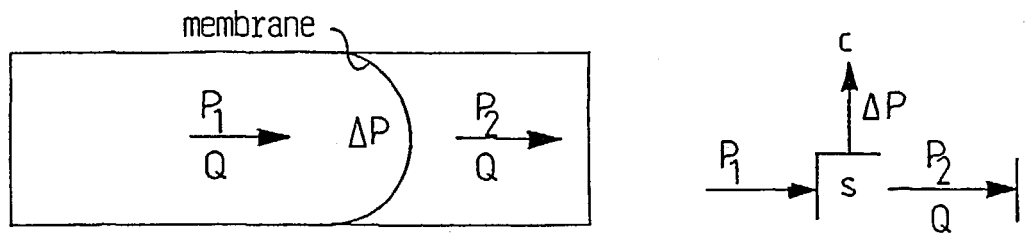
Figure 7B:
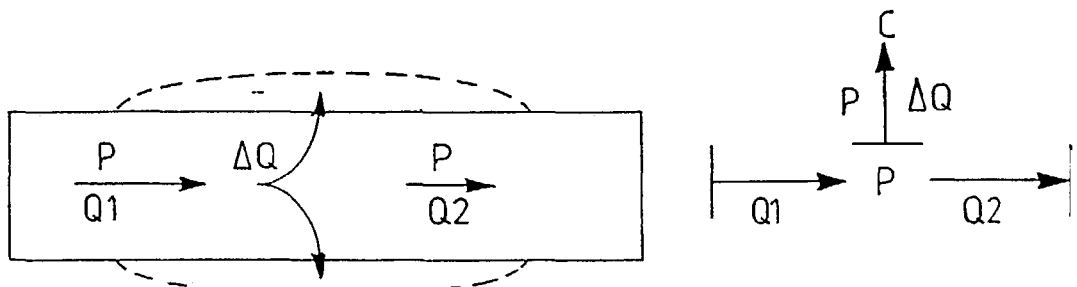
Figure 8A:
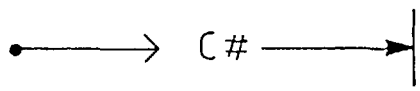
Figure 8B:
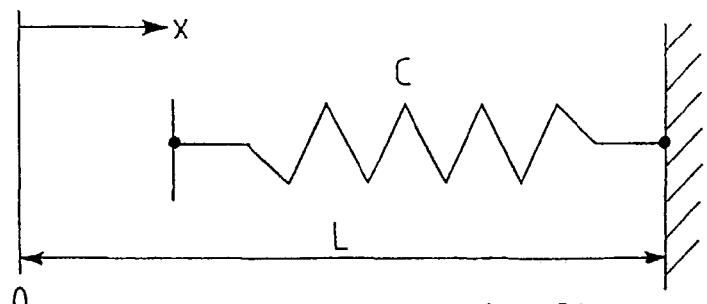
Figure 9A:
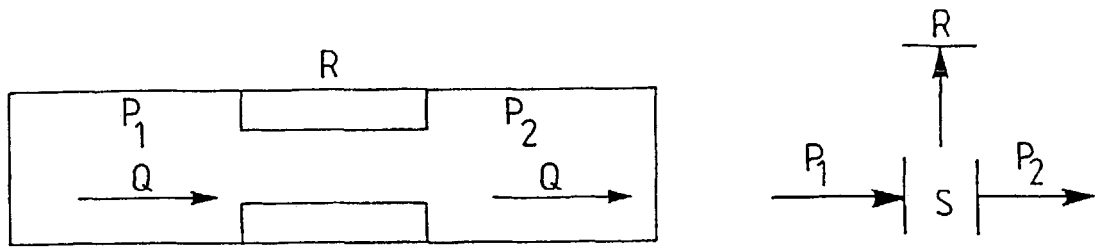
Figure 9B:
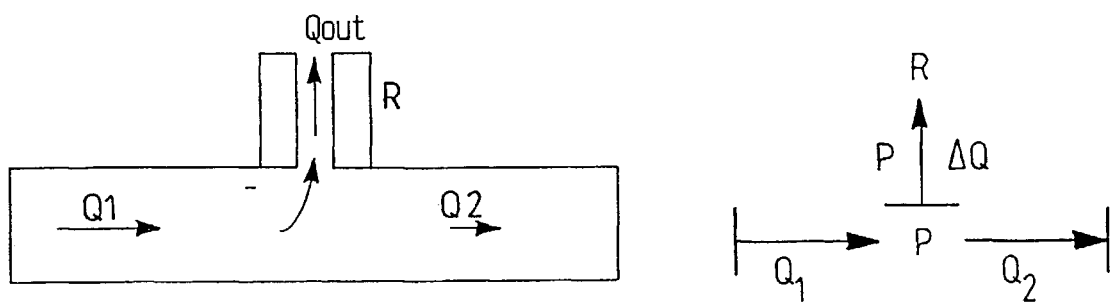
Figure 10:
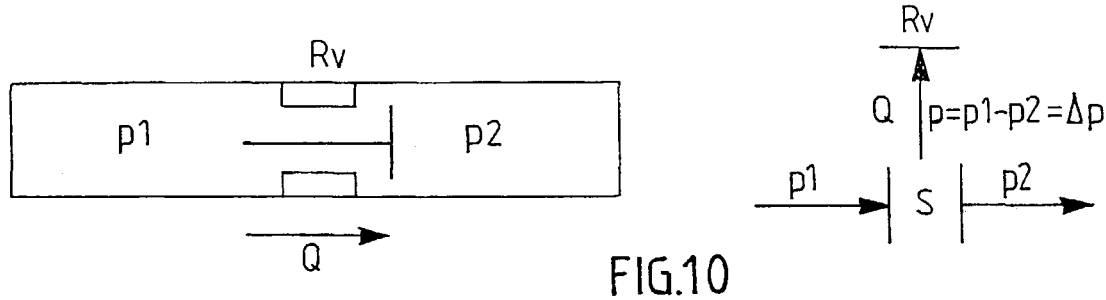
Figure 11:
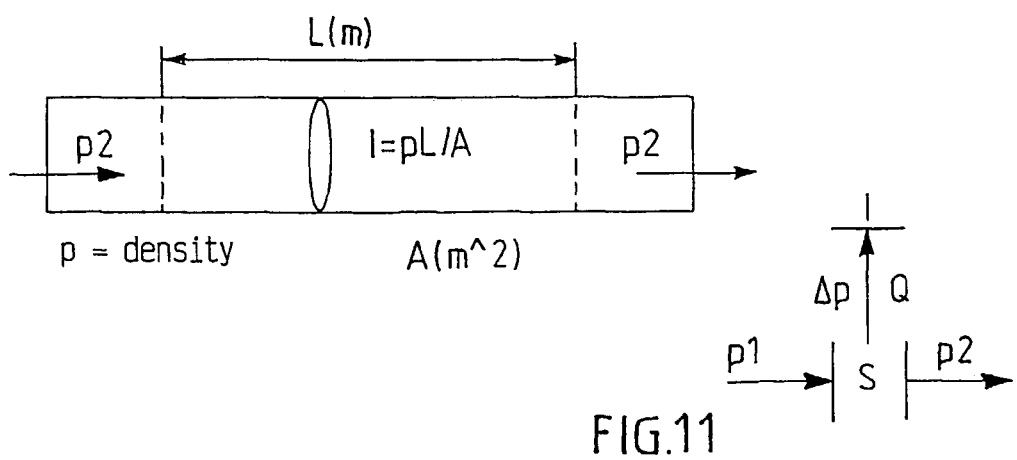
Figure 12:
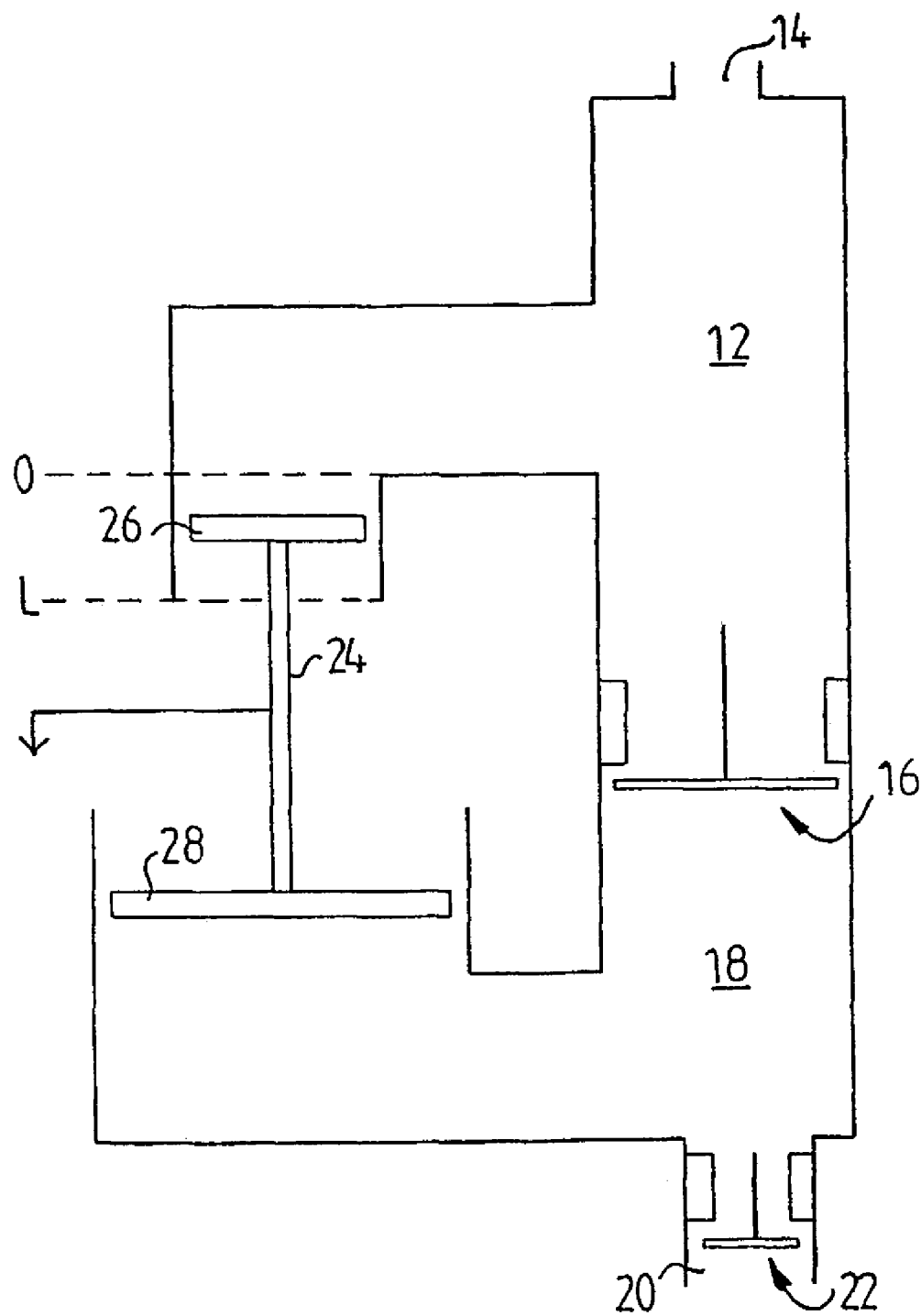
Figure 13:
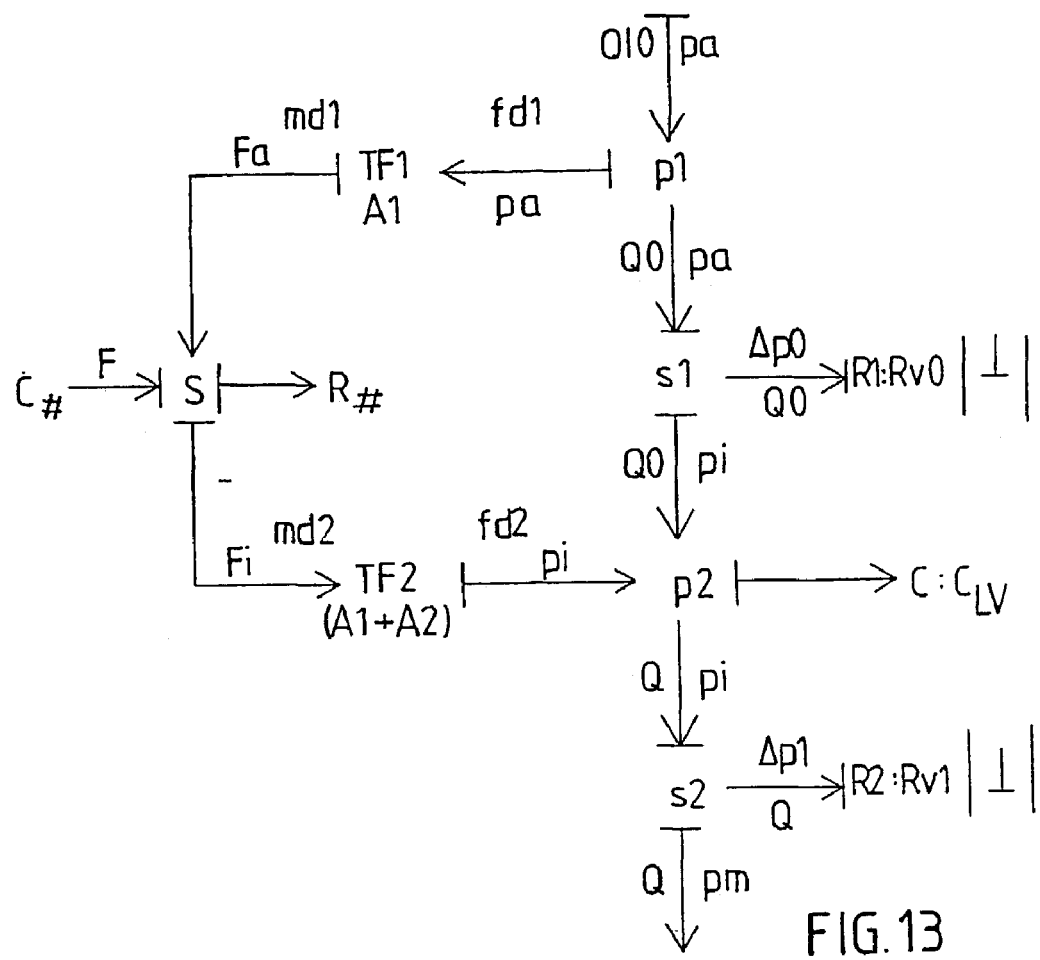
Figure 14:
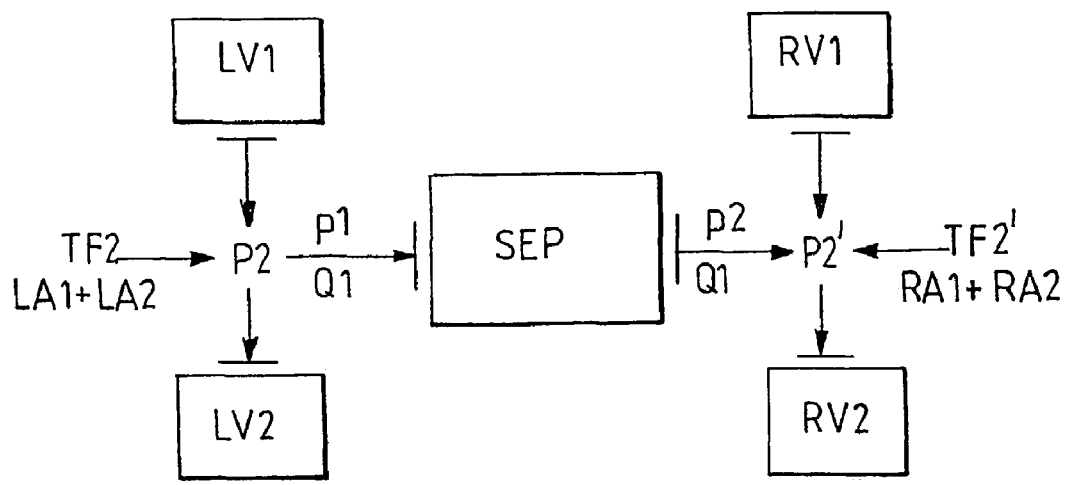
Figure 15A:
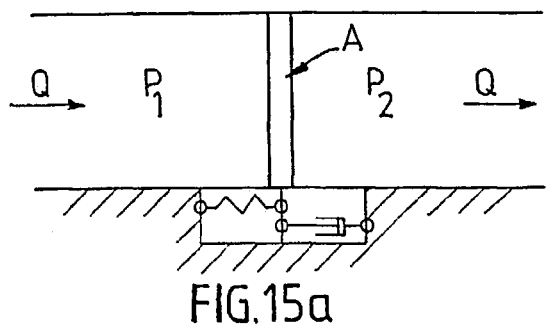
Figure 15B:
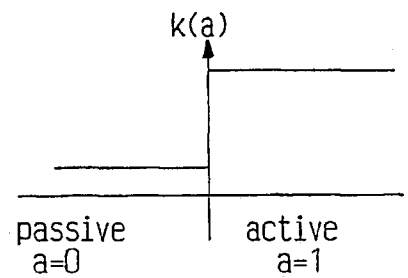
Figure 15C:
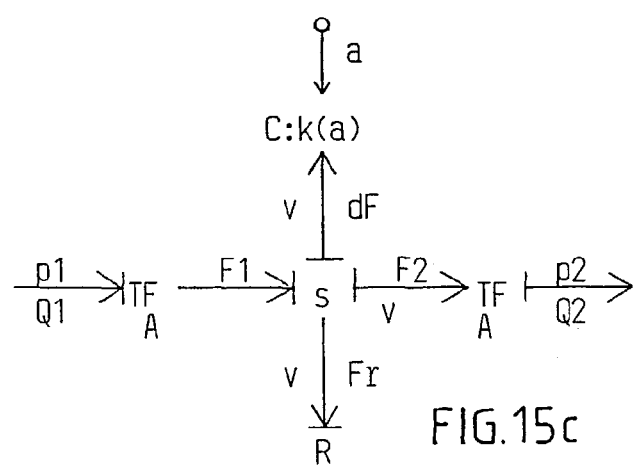
Figure 16A:
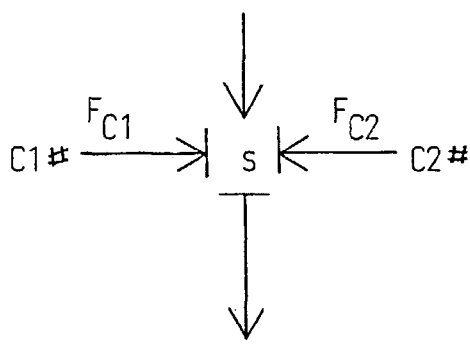
Figure 16B:
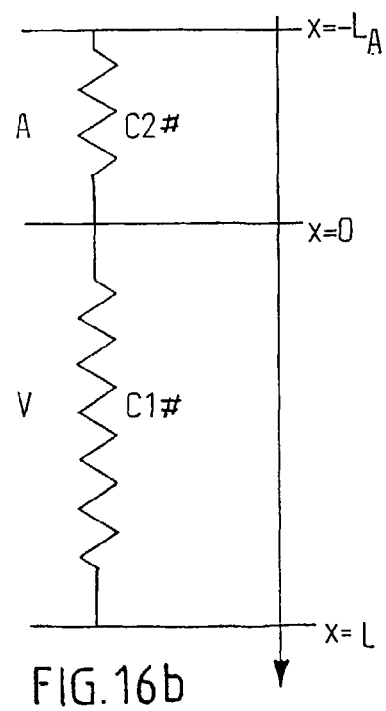

FIGS. 1a and 1b illustrate the basic principles of a ΔV-pump;
FIGS. 2a-2d illustrate different stages of the pumping process a ΔV-pump with low pumping frequency;
FIGS. 3a-3d illustrate different stages of the pumping process a ΔV-pump with high pumping frequency;
FIGS. 4a and 4b illustrate a TF-element;
FIG. 5 illustrates the principles of an S-junction;
FIG. 6 illustrates the principles of a P-junction;
FIGS. 7a and 7b illustrate a C-element in a flow system;
FIGS. 8a and 8b illustrate a controllable C-element;
FIGS. 9a and 9b illustrate an R-element in a flow system;
FIG. 10 illustrates a controllable R-element;
FIG. 11 illustrates an I-element in a flow system;
FIG. 12 shows an equivalent model of the ΔV-pump;
FIG. 13 shows the bond graph corresponding to the equivalent model of the ΔV-pump;
FIG. 14 shows a block diagram illustrating the principles of the bond graph of two mutually cooperating representations of the ΔV-pump, and
FIGS. 15a-15c illustrate different aspects of modeling the ventricular septum.
FIGS. 16a and 16b illustrates a bond graph showing a preferred embodiment of a section of the bond graph shown in FIG. 13.

DETAILED DESCRIPTION OF PREFERRED EMBODIMENTS OF THE INVENTION

Below is a description, with references to accompanying drawings, of different elements used in the bond graph system. It should be noted that the description is limited to mechanical and flow systems, but the corresponding elements are also applicable for electrical and thermal systems.

TF-element: TF stands for transformation and the element is used to connect different physical domains, e.g a flow domain and a mechanical domain. The designation of the TF-element is disclosed in FIGS. 4a and 4b where the force F/velocity v on one side of a pump with a piston and connected with pressure p/flow Q on the other side via area parameter A as $F=p \cdot A$ and $v=Q/A$.

S-junction: An element or a point in a flow system or in a mechanical system represented by an S-junction (a serial element/point) has a constant flow/velocity and the sum of pressure/force in the point is zero. In a flow system is thus the flow constant whereas the pressure can vary. FIG. 5 illustrates the principles of an S-junction.

P-junction: An element or a point in a flow system or in a mechanical system represented by a P-junction (a parallel element/point) has a constant pressure/force and the sum of flow/velocity is zero. In a flow system is thus the pressure constant whereas the flow can vary. FIG. 6 illustrates the principles of a P-junction.

S and P-junctions might be considered to represent different physical states in a system having a characterizing flow, force etc. S and P-junctions can be influenced in many different ways by applying a certain pressure, by applying losses due to resistance etc. These influences are designated by different elements where each designates a specific type of influence. Examples of the most commonly used influencing elements are given below.

C-element: A C-element is an element with the capability to store or supply a certain physical parameter in a certain system, e.g. a tank in a flow system or a spring in a mechanical system. FIGS. 7a and 7b illustrate a C-element in a flow system. In FIG. 7a the C-element is connected to an S-junction, which physically corresponds to a membrane in a pipe. In FIG. 7b is the C-element connected to a P-junction, which physically corresponds to elasticity in the walls of a pipe.

The mathematical relationship for a C-element in a flow system is $$p = \frac{1}{C} \int Q dt,$$

where p designates the pressure, Q the flow and C a constant. If C is high, the C-element corresponds to a very elastic element, cf. a weak spring, and if C is low, the C-element is less elastic, cf. a strong spring. In order to simulate a power source for the ΔV-pump a controllable C-element is used. When simulating a muscle contraction it is important to take into account that the force excerted by the muscle is largest in the beginning of a contraction and decreases as the muscle contracts. As indicated in the bond-graph (see FIG. 8b) the muscle is arranged on the mechanical side by means of a C-element having a mechanical equivalence in a spring having a changeable spring constant. This is possible by the controlled C-element where a parameter C# changes in dependence of if the muscle is active (C# has a low value) or inactive (C# has a high value). The controllable C-element is illustrated in FIGS. 8a and 8b and is modeled by the following equation:

$$Fc = \frac{1}{C\#}\left(L - \int v\,dt\right) = \frac{1}{C\#}(L - x), \text{ whereas}$$

Fc is the force excerted by the C-element;
L is the maximal length of a stroke;
x is the distance to a zero level, which in the mathematical model of the heart is the distance between the present level and the level during diastole for the plane of the heart valves;
C# (passive)=Cp (high value), and
C# (active)=Ca (low value).

R-element: An R-element is a resistance element that corresponds to losses in a system due to e.g. friction or constrictions. Connecting an R-element to an S-junction corresponds physically to a constriction of the pipe, see FIG. 9a. If an R-element is connected to a P-junction this physically corresponds to an outflow port from the P-junction (a pipe). The mathematical relationship for an R-element in a flow system is p=Q*R, where p designates the pressure, Q the flow and R a constant of the system.

A non-linear R-element may be used to designate a non-return valve. If the above relationship is written as Q=p/R a non-return valve may be modeled as Q=p/R if p>=k and Q=0 for p<k. If k is negative then there is back-flow in the valve.

FIG. 10 illustrates a non-return valve Rv and a corresponding bond-graph of a non-return valve. The non-return valve might alternatively be modeled as $p=R*Q^2$, i.e. the pressure is proportional to the square of the flow. Using this relationship the non-return valve may be modeled as $$Q = \text{sign}(\Delta p)\sqrt{\left|\frac{p}{R}\right|} \text{ if } p >= k$$

and Q=0 for p<k. Sign($\Delta p$)=−1 if $\Delta p$<0 or 1 if $\Delta p$>=0.

I-element: Designates intensity storing elements storing e.g. kinetic energy, corresponding to inductance in an electrical system or to a long pipe in a flow system. The mathematical relationship for the I-element is:

$$Q = \frac{1}{I}\int p\,dt,$$

where Q designates the flow, p the pressure and I a constant of the flow system. FIG. 11 shows an I-element connected to an S-junction in this case illustrating a long pipe filled with flowing liquid having a certain amount of kinetic energy. In the figure L designates the length of a section of the pipe, A represents the cross-sectional area of the pipe, p1 and p2 represent pressures and ρ the density of the fluid.

In order to illustrate the principles of the bond graph outlined in relation with FIG. 13 an equivalent model of the ΔV-pump is described with references to FIG. 12.

The model of the system comprises an upper chamber 12 having an inflow opening 14 where a fluid flows into the upper chamber 12. A first non-return valve 16 separates the upper chamber from a lower chamber 18. The lower chamber has an outflow opening 20 provided with an outflow non-return valve 22. Reciprocating piston pump means 24 performs the pumping action. The piston pump means comprises a first piston 26 with an area A1 and in connection with the upper chamber 12, and a second piston 28 with an area A1+A2 in connection with the lower chamber 18. The first and second pistons are mechanically connected to each other and adapted to perform a reciprocating movement from the level designated with "0", in relation to the first piston 26, to level L and back to 0. An external power source force the piston pump means 24 down from the 0-level and is released when the L-level is reached. The flow entering the lower chamber via the non-return valve 16 forces the piston pump means back to the 0-level.

When the force from the external power source starts to move the piston pump means down, the pressure inside the lower chamber increases and when that pressure is higher than the pressure below the outflow valve 22 the valve opens and fluid is expelled. The pressure in the lower chamber decreases due to the outflow and when that pressure is lower than the pressure in the upper chamber the valve 16 opens and fluid flows into the lower chamber. Due to that inflow the pressure increases and forces, as indicated above, the piston pump means to the 0-level again.

As illustrated in FIG. 12 the area of the first piston facing the upper chamber is smaller than the area of the second piston facing the lower chamber. This is very important in order to achieve the pumping action or more precisely to have the piston pump means to return to the 0-level when the force is released.

A computer-based system adapted to create a representation of the mechanical and flow-mechanical function of a ΔV-pump is arranged using a mathematical modeling algorithm based upon a transforming element adapted to connect different physical domains via a transforming value.

The modeling of a transforming element is described in detail above.

Below is a description of a computer based system for modeling of a ΔV-pump.

The system, illustrated with references to FIG. 13, comprises an upper transforming element TF1 and a lower transforming element TF2 each having a flow domain, fd1 and fd2, respectively, and a mechanical domain, md1 and md2, respectively. The upper transforming element TF1 is provided with a transforming value A1 and the lower transforming element TF2 is provided with a transforming value A1+A2, wherein A1 and A2>0.

The upper and lower transforming elements are interconnected in an S-junction such that their mechanical domains md1, md2 are connected. The mechanical domains are provided with a control value representing a measure (F) arranged to intermittently and simultaneously activate said mechanical domains of the transforming elements.

The measure represents a net force F from an external power source (not shown), in the model implemented as a non-linear C-element (C#). The S-junction is also provided with a non-linear R-element (R#) that represents damping or a movement restriction.

In FIG. 13 pi and pa indicate pressure-parameters in the flow domains of the upper and lower transforming elements, respectively and Fa and Fi indicate force-parameters in the mechanical domains. In order to simplify the figure indications of velocity and some of the flow indications are omitted.

The pumping action is achieved by the force represented by F, Fa and Fi, wherein Fa=pa·A1 and Fi=pi·(A1+A2). Fa is a value representing the force excerted on the mechanical domain of the upper transforming element, and Fi is a value representing the force excerted on the mechanical domain of the lower transforming element.

According to a preferred embodiment of the invention the flow domains of the upper and lower transforming elements are separated by a first S-junction S1 having the flow domain of the upper transforming element upstreams and having the flow domain of the lower transforming element downstream. A second S-junction S2 is provided at the outflow of the flow domain of the lower transforming element. The S-junctions represent bounderies between domains, in this case between the upper and lower chambers and the lower chamber and downstream, respectively, of the equivalent model of the system. The non-return valves are implemented by R-elements, R1, R2. First and second P-junctions, P1, P2 respectively, represent the situation in the upper and lower chambers, respectively, of the equivalent model of the system.

In FIG. 13 designates
Pi the ventricular pressure;
Pa the pressure above the valveplane;
Pm the pressure below the outflow valve;
$\Delta p0 = Pi - Pm$;
$\Delta p1 = Pa''Pi$;
QI0 the inflow;
Q0 the flow through the valve;
Q the outflow;
$C_{LV}$ is an elasticity parameter of the ventricular wall;
Rv0, Rv1 represents flow resistance in relation to the valves;

A description of mutually connected models of pumps in order to be able to simulate a heart in its entirety is made below with references to FIG. 14. According to a preferred embodiment of the invention is the computer-based system adapted to create a representation of a heart that comprises two mutually cooperating representations of the ΔV-pump as described above. A schematic block diagram illustrates in a simplified manner the connection between two ΔV-pumps. The connection is accomplished between the two P-junctions, P2, P2' connected to the flow domains of two transferring elements TF2, TF2'. The interconnection point is designated SEP (as in septum). The non-return valves upstream and downstream enclosing the P-junctions in the left and right pump, respectively, are designated LV1, LV2, RV1 and RV2. The transforming values for the transforming elements TF2 and TF2' are designated LA1+LA2 and RA1+RA2, respectively, where L and R represent the left and the right side of the heart.

The ventricular septum of the heart is the wall between the left and the right ventricles of the heart. This wall is very elastic and movable when the heart muscle is inactive (during diastole) but turns very stiff when the muscle is active (during systole). This implies that the ventricular septum has a controlling function between the ventricles. This is implemented in the mathematical model as a controlling function between the two interconnected ΔV-pumps. In the bond-graph model the ventricular septum is represented by a controlled C-element (representing an elastic physical parameter), and an R-element.

FIG. 15a shows an equivalent illustration of the ventricular septum where the septum SEP is a membrane-like object provided with a non-linear spring and a damper, the spring constant is small when the septum is passive and higher when active, this is illustrated in FIG. 15b. The corresponding bond-graph is disclosed in FIG. 15c. Two transforming elements TF are arranged to model the connection from the flow system of the left ventricle, via the mechanical system of the septum, which is modeled by an S-junction where the C-element and R-element are connected, to the flow system of the right ventricle. The C-element is controlled by a parameter k(a) that is varied according to FIG. 15b. The area of the septum is a parameter (not shown in the figure) used by the transforming elements.

FIG. 16a discloses a bond graph section of a preferred embodiment of the force generating part of the bond graph shown in FIG. 13 (the S-junction to the left in FIG. 13). Herein is the force F divided into $F_{C1}$ representing the contribution from the ventricle and $F_{C2}$ representing the contribution from the atrium. The non-linear R-element R# is shown in FIG. 16a. As mentioned in relation with the description of the bond graph in FIG. 13 the R-element represents damping or a movement restriction. If modeling a heart the R-element may be used to simulate different pathological states, e.g. pathological non-synchronism of the heart e.g. due to wrong timing of depolarization or repolarization of the heart muscle.

FIG. 16b shows an equivalent illustration of the bond graph section disclosed in FIG. 16a.

The controllable C-elements illustrated in FIGS. 16a and 16b are modeled by the following equations:

$$Fc1 = \frac{1}{C1\#}\left(L - \int v\,dt\right) = \frac{1}{C1\#}(L - x), \text{ and}$$

$$Fc2 = -\frac{1}{C2\#}\left(L_A + \int v\,dt\right) = -\frac{1}{C2\#}(L_A + x), \text{ whereas}$$

Fc1 is a force related to the ventricular contraction;
Fc2 is a force related to the atrial contraction;
L is the maximal length of a ventricular stroke;
$L_A$ is the maximal length of an atrial stroke;
x is the distance to a zero level, which in the mathematical model of the heart is the distance between the present level and the level during diastole for the plane of the heart valves;
C1# (passive)=C1p (high value),
C1# (active)=C1a (low value),
C1# (physical limitation)=C1c (low value).
C2# (passive)=C2p (high value),
C2# (active)=C2a (low value),
C2# (physical limitation)=C2c (low value).

Before the pumping action of the pump is simulated the mathematical model must be initialized.

As indicated above many different parameters may be used as input values. According to a preferred embodiment of the invention A2 is set to a value of 0.2*A1.

According to another preferred embodiment of the invention A2 is dynamically changed during the pumping cycle.

According to still another embodiment of the invention the relationship between A1 and A2 is changed during the pumping cycle.

Also parameters of the different elements represented in the bond-graph must be set in accordance with the intended use.

The model of a ΔV-pump as described in relation to the bond graph is then used as a basis for simulating the pumping action. A commercially available simulation program such as "Simulink" from MathWorks Inc preferably performs this simulation. The process of transforming a bondgraph to equations is described in Gawthrop, Peter and Smith, Lorcan "METAMODELING: Bond graphs and dynamic systems"; Prentice Hall. Transforming the equations into a block representation adapted for use in Simulink is a straightforward operation that is described in detail in e.g. "Mastering Simulink 2" by Dabney, James B and Thomas, L.; Prentice Hall.

Many different applications are possible for the representation of the pump and the combined pump representation modeling a heart.

According to one preferred application is a representation of the heart used for analytic, diagnostic and therapeutic purposes. In such an application the representation might be stored on a computer and being publicly available via e.g. the Internet. Different input data obtained from a patient are then applied into the system. These data could be measured or determined by the patient at home or anywhere where transmission equipment is available for transmitting the data to the computer running the system. Among data applied into the system can be mentioned blood pressure data, heart rate, parameters related to any pathological state, medication affecting the pumping of the heart, etc.

According to another application of the computer-based system is the representation stored and used in an implantable heart stimulator or defibrillator for controlling various functions of the implanted device, e.g. to change stimulation mode, to perform diagnosis based upon sensed conditions, etc.

Below is a description of the underlying medical background theory, which is provided in order to increase the understanding of the basic principles of the invention.

The frequency variation of the heart is significant (approximately between 60 and 200 beats per minutes) and because of that, different mechanisms optimize the $\Delta V$-volume in dependence of the frequency. Since the $\Delta V$-volume is coupled to the motion of the valve plane there has to be mechanisms that change the $\Delta V$-volume in order to speed up the return of the valve plane, e.g. higher frequencies acts with smaller $\Delta V$-volumes.

Because the heart is embedded in an environment that, especially at high frequencies, prevents larger changes of the form of the heart, the mechanism that minimizes the outer volume change is achieved by dividing the $\Delta V$-volume in two parts, $\Delta V$-external and $\Delta V$-internal. $\Delta V$-external and $\Delta V$-internal is related to the valve-plane in order to contribute to its returning movement, automatic control and closing, of the valves without back-flows.

Below is a discussion of important features for these two volume parts.

$\Delta V$ external is the difference in volume between the smallest and the largest heart volume during a heart cycle. The decrease of the volume occurs when the valve plane moves towards apex. The main volume decrease is occurred by the suction created above and in the surroundings of the valve-plane when it is drawn towards apex. This part of the total $\Delta V$ function and the contribution from the great vessels give a smooth function of the inflow to the heart. $\Delta V$ external is largest at lower frequencies when the diastolic time (blood filling phase) is long and the kinetic energy is low. The dynamic pressure is close to zero. The static filling-pressure increases and is the power-source for the total increase of the volume of the heart. The largest volume increase occurs, due to physical laws, in the zone of the heart having the largest cross-sectional area, i.e. in the mid-zone of the egg-shaped were the valve plane motion are. The valve-plane has a rigid structure and would counteract an expansion of the heart in this region. However, around the valve-plane a fastening arrangement is provided that elastically fasten the valve-plane to the inner heart walls. This arrangement takes place in the area called sucus coronarius. During expansion of the mid-zone the fastening arrangement is bent against the valve-plane and thereby increasing its area. The conical shape (egg-shape) of the heart results in that the valve-plane during expansion even further moves in a direction away from apex. The motion of the valve plane stops when the cross-sectional area of the atria overrides that of the ventricles. Because of that one can see ringing motions of the valve plane when it reaches its 'zero position' on the way to move the AV-plane away from apex from this zero postion. By the contraction of the atria it pulls the AV-plane away from apex and in the same time and thereby make an internal redistribution of the blood. At last the pericardium will slow down the expansion. Because of that, the valve-plane is able to enclose an even larger blood-volume in the forthcoming systole.

During systole the heart has a larger valve-plane (expanded according to the above-mentioned description) and a longer length of stroke. The very slow flowing incoming blood-flow will now be caught by the movement down of the valve-plane with the consequence that $\Delta V$ external decreases and gives a pressure- and flow-leveling of the incoming flow. This applies also for the incoming vessels, i.e. vena cava inferior, vena cava superior and the four pulmonary veins. If the heart frequency not increases the procedure will be repeated.

In higher frequencies and increasing dynamics the diastolic time will be very short compared to the systolic time. There will be less time left for the slow static filling phase and the atrial contraction will follow directly on the fast filling phase. The heart will now have the possibility to reduce the total $\Delta V$-volume by reducing the external $\Delta V$-volume.

The $\Delta V$-internal function will know be described in greater detail. When working in higher frequencies the heart creates, because of the back- and forth going movements of the valve-plane, an increasing amount of kinetic energy in to and out from the heart. The increased kinetic energy can now produce more power per $cm^2$. The presumption is that incoming flow must go somewhere when the valve-plane prepares the next pumping action. Fast external volume changes would, due to the mass and the inertia in the environment of the heart, lead to increasing resistance and filling pressure. Instead of wasting volume and energy on the external $\Delta V$-volume the heart will try to stay in its largest size and the incoming flow will be concentrated on the internal $\Delta V$-volume. This is arranged in the following way:

In the valve plane is located, apart from the four heart valves, also the two large outgoing blood vessels, aorta and truncus pulmonalis. These vessels must follow the movement of the valve-plane that in normal cases is about 22 mm. To achieve this aorta is provided with a "duplicating part" (about 10 mm) of the pericardium, involving that aorta is able to move as a piston in to and out from the pericardium without stretching it. Furthermore, the helix-form of aorta ascendens and arcus aortae eases this back- and forth-movements. The heart straightens the helix by 10-degree rotation in its length axis.

The movement of aorta in to and out from of the pericardium gives a $\Delta V$-volume that equals the cross-sectional area of aorta multiplied with the length of stroke for the valve plane which results in a $\Delta V$-volume of about 15 ml. The contribution from truncus pulmonalis is a bit uncertain but would probably be 5-10 ml. $\Delta V$-internal consists of these two volumes and is always available. $\Delta V$-internal varies in relation with the length of stroke and has a size that, at higher frequencies during the fast filling phase, allows the valve plane to return and at the same time allows a flowing through.

The present invention is not limited to the above-described preferred embodiments. Various alternatives, modifications and equivalents may be used. Therefore, the above embodiments should not be taken as limiting the scope of the invention, which is defined by the appendant claims.

The invention claimed is:

1. A system comprising including:
a processor,
a memory,
a display,
flow-mechanical input data,
a ΔV-pump model,
wherein the ΔV-pump model comprises;
an upper transforming element (TF1) and a lower transforming element (TF2), each having a flow domain (fd1, fd2) and a mechanical domain (md1, md2), the upper transforming element is provided with a transforming value A1 and the lower transforming element is provided with a transforming value A1+A2, wherein A1 and A2>0, the upper and lower transforming elements are interconnected such that their mechanical domains are connected, said mechanical domains are provided with a control value representing a measurement arranged to intermittently and simultaneously activate said mechanical domains of the transforming elements and that the flow domains of the upper and lower transforming elements are separated by a first non-return valve element (R1) having a flow domain of the upper transforming element upstream and the flow domain of the lower transforming element downstream,
wherein the processor processes the flow mechanical input data and generates a changed ΔV-pump model, and the display displays the changed ΔV-pump model.

2. The system according to claim 1, wherein said ΔV-pump model further comprises said measurement representing a net force (F) being from a power source.

3. The system according to claim 2, wherein said ΔV-pump model further comprises a pumping action achieved by said net force (F) being represented by F+Fa−Fi, wherein Fa=pa·A1 and Fi=pi·(A1+A2), wherein
Fa is a value representing the force exerted on the mechanical domain of the upper transforming element;
Fi is a value representing the force exerted on the mechanical domain of the lower transforming element;
pa represents the pressure in the flow domain of the upper transforming element, and pi represents the pressure in the flow domain of the lower transforming element.

4. The system according to claim 2, wherein said ΔV-pump model further comprises said net force (F) as being a resulting force of Fc1 and Fc2, wherein Fc1 is a force related to a ventricular contraction and Fc2 is a force related to an arterial contraction.

5. The system according to claim 1, wherein said ΔV-pump model further comprises a second non-return valve element is provided at an outflow of the domain of the lower transforming element.

6. The system according to claim 1, wherein said ΔV-pump model further comprises said connection of the mechanical domains of the transforming elements is provided with a non-linear R-element representing damping or a movement restriction.

7. The system according to claim 1, wherein the display of the ΔV-pump model is adapted to represent a heart wherein the representation of the heart comprises two mutually cooperating representations of a ΔV-pump.

8. The system according to claim 7, wherein the ΔV-pump model representation of a heart includes a ventricular septum as represented by two transforming elements controlled by a C-element.

9. The system according to claim 7, wherein said created representation of the heart is used for at least one of the following, analysis, diagnosis or therapy of a heart.

10. The system according to claim 1, wherein said display of a ΔV-pump model is remotely accessible via a commonly available network.

11. The system according to claim 9, wherein the analysis, diagnosis and therapy is to control an implanted defibrillator or pacemaker.

12. The system according to claim 10, wherein the commonly available network is an Internet.

* * * * *